United States Patent
Anderson et al.

(10) Patent No.: US 10,856,733 B2
(45) Date of Patent: Dec. 8, 2020

(54) METHODS AND SYSTEMS FOR TESTING ASPECTS OF VISION

(71) Applicants: Luke Anderson, Porthcawl (GB); Stephanie Campbell, Bristol (GB)

(72) Inventors: Luke Anderson, Porthcawl (GB); Stephanie Campbell, Bristol (GB)

(73) Assignee: OKULO Ltd., Bristol (GB)

( * ) Notice: Subject to any disclaimer, the term of this patent is extended or adjusted under 35 U.S.C. 154(b) by 18 days.

(21) Appl. No.: 15/580,736

(22) PCT Filed: Jun. 13, 2016

(86) PCT No.: PCT/GB2016/051749
§ 371 (c)(1),
(2) Date: Dec. 8, 2017

(87) PCT Pub. No.: WO2016/198902
PCT Pub. Date: Dec. 15, 2016

(65) Prior Publication Data
US 2018/0140178 A1    May 24, 2018

(30) Foreign Application Priority Data
Jun. 12, 2015 (GB) .................................. 1510242.9

(51) Int. Cl.
*A61B 3/10* (2006.01)
*A61B 3/00* (2006.01)
(Continued)

(52) U.S. Cl.
CPC ............ *A61B 3/005* (2013.01); *A61B 3/0058* (2013.01); *A61B 3/022* (2013.01); *A61B 3/024* (2013.01);
(Continued)

(58) Field of Classification Search
CPC ..... A61B 3/0041; A61B 3/032; A61B 3/0033; A61B 3/005; A61B 3/02; A61B 3/024;
(Continued)

(56) References Cited

U.S. PATENT DOCUMENTS 5,206,671 A    4/1993  Eydelman et al.
5,920,374 A    7/1999  Vaphiades et al.
(Continued)

FOREIGN PATENT DOCUMENTS

| DE | 102014116665 A1 | 3/2016 |
|---|---|---|
| WO | WO2013/096473 A1 | 6/2013 |
| WO | WO2016/198902 A1 | 12/2016 |

OTHER PUBLICATIONS

"A Pilot Study Evaluating the Use of EyeSpy Video Game Software to Perform Vision Screening in School-Aged Children", Rupal H. Trivedi et al., Journal of AAPOS, vol. 14 No. 4, pp. 311-316, , Aug. 2010.

(Continued)

*Primary Examiner* — Brandi N Thomas
(74) *Attorney, Agent, or Firm* — Gordon & Jacobson, P.C.

(57) ABSTRACT

The invention provides an advantageous system and corresponding method for measuring a plurality of aspects of vision. It is a computer-implemented, user-interactive system which can be used by practitioners such as opticians to measure and assess a patient's visual acuity. It comprises a handheld computing device arranged and configured to present at least one optotype to a user (patient) within a gamified environment. This aspect of the invention provides the advantage that it is more easily used by certain types of patients, such as children, the elderly or those suffering from medical/clinical conditions who would typically struggle to use traditional measuring tools. In a preferred embodiment, the optotype has at least one characteristic selected to (Continued)

facilitate the measurement of at least one, or preferably at least two, aspects of visual function; and the invention is arranged to detect the user's response to the optotype to provide a measurement of at least one or at least two aspects of visual function. Advantageously, this can be achieved in one 'sitting'. The plurality of aspects of visual function can include visual acuity, central visual field, contrast sensitivity, stereopsis and/or colour vision, detection acuity of vision, resolution acuity of vision (spatial resolution or identification of static of dynamic directionality), recognition acuity of vision, hyperacuity of vision, temporal acuity of vision, spectral acuity of vision. The at least one optotype is repeatedly presented to the user, and the at least one characteristic is altered upon each repetition. The repetition may continue until a threshold or limit is reached. The at least one characteristic relates to the level of detail, contrast, colour, position or movement of the at least one optotype.

25 Claims, 2 Drawing Sheets (51) Int. Cl.
*A61B 3/032* (2006.01)
*A61B 3/103* (2006.01)
*A63F 13/213* (2014.01)
*A63F 13/2145* (2014.01)
*A63F 13/215* (2014.01)
*A63F 13/85* (2014.01)
*A61B 3/02* (2006.01)
*A61B 3/024* (2006.01)
*A61B 3/06* (2006.01)
*A61B 3/08* (2006.01)
*A61B 3/113* (2006.01)
*A61B 3/18* (2006.01)
*A61B 5/11* (2006.01)
*A61B 5/00* (2006.01)

(52) U.S. Cl.
CPC .............. *A61B 3/032* (2013.01); *A61B 3/066* (2013.01); *A61B 3/08* (2013.01); *A61B 3/103* (2013.01); *A61B 3/113* (2013.01); *A61B 3/18* (2013.01); *A61B 5/1114* (2013.01); *A61B 5/6898* (2013.01); *A63F 13/213* (2014.09); *A63F 13/215* (2014.09); *A63F 13/2145* (2014.09); *A63F 13/85* (2014.09)

(58) Field of Classification Search
CPC ....... A61B 3/028; A61B 3/0091; A61B 3/066; A61B 3/08; A61B 3/10; A61B 3/113; G02B 27/2214; G02B 27/2264; G02B 1/04; G02B 1/041
USPC ......... 351/200, 205, 206, 209–211, 221, 222
See application file for complete search history.

(56) References Cited

U.S. PATENT DOCUMENTS

| | | |
|---|---|---|
| 2008/0309880 A1 | 12/2008 | Fisher et al. |
| 2010/0195051 A1 | 8/2010 | Murray et al. |
| 2013/0083185 A1 | 4/2013 | Coleman, III |
| 2013/0128229 A1 | 5/2013 | Huang |
| 2013/0141697 A1 | 6/2013 | Berry et al. |
| 2013/0155376 A1* | 6/2013 | Huang ................. A61B 3/024 351/224 |
| 2014/0211166 A1 | 7/2014 | Scherlen et al. |
| 2014/0211167 A1 | 7/2014 | Lewis |

OTHER PUBLICATIONS

Office Action dated May 26, 2020 of JP Application No. 2018-516643.
Nintendo, Practicing Your Visual Acuity DS Eye training: Training Software to Train Your Visual Acuity, downloaded Jul. 6, 2020, available at https://www.nintendo.co.jp/ds/ag3j/trainingsoft/index.html.

* cited by examiner

METHODS AND SYSTEMS FOR TESTING ASPECTS OF VISION

CROSS-REFERENCE TO RELATED APPLICATIONS

This application is the national stage of International Patent Application No. PCT/GB2016/051749 filed on Jun. 13, 2016, and which claims priority to British Patent Application Nos. GB 1510242.9 filed on Jun. 12, 2015, all of which are hereby incorporated by reference in their entireties as if fully set forth herein.

BACKGROUND

1. Field

This invention relates generally to measuring and testing aspects of vision and visual function in individuals, and more particularly to computer-implemented tools and solutions for such purposes. The invention is particularly suited, but not limited to, use in measuring aspects of vision and visual function in individuals who do not have well developed communication skills, or have difficulty in concentrating for sustained periods of time e.g. children.

2. Related Art

The measurement of vision and visual function are vital components to understanding the health status of a patient's eyes and visual system, and to understanding if they require visual correction or medical intervention.

It is vital that the measurement of vision is as accurate as possible in order to identify any eye or brain disease at the earliest opportunity, so that treatment can be started promptly. This is particularly difficult in the case in children and in elderly patients, where results of vision testing are inherently more variable. If a loss of vision goes undetected, it may in some cases quickly result in blindness. This can bring with it huge personal, social and economic consequences.

Understanding visual function is a cornerstone of two medical specialities: ophthalmology and neurology. A device is presented that measures not just standard visual acuity (synonymous with the letter chart) and contrast, but measures wider visual function in a manner that provides not just optical information, but information on neural processing of information from within the brain itself, 'visual function'. The presented device provides an indication of visual function that would otherwise only be available from equipment in specialist hospital clinics and vision labs.

The measurement of vision is fraught with difficulty due to limitations of testing charts and due to the variability of the attention span of patients themselves. Initially, when big stimuli such as letters or symbols are presented, they are easily seen and identified, and motivation is high. Typically, vision is measured using recognition of letters on a Snellen eye chart. When progressing to the smaller letters or symbols during a vision test, they become less easy to see, and the patient becomes less confident. If attention drops off, a poorer level is recorded, and the clinician does not know if this is due to poor attention, or due to an underlying vision problem.

The visual "threshold" is the point at which the patient is able to just see, or just misses, the stimulus being presented. However, near-threshold testing is the period where attention most often wanders, and yet this is the point at which attention is most important in order to gain a reliable measurement of vision. The 'threshold' of vision is only tested once or twice in a traditional chart test. Subjects must have their vision measured multiple times in order to gain a reliable result, and the standard process for doing so is time-consuming and poorly stimulating, it often requires repeat hospital visits. It is not suitable for use in a fast-paced clinical environment, and less so for individuals with poor understanding or communication abilities. Currently, there is no reliable method of home-monitoring of vision.

Despite the popularity and stereotypy of the Snellen chart, this particular method of vision testing is not a comprehensive examination of visual function. There are many types of visual attributes that combine in order to allow an individual to perceive the world in a normal manner, which are not reflected in the correct perception of the Snellen/log MAR 'Visual Acuity' chart. One obvious example is that of defective colour vision whereby despite a perfect score on a typical eye chart, the patient may be profoundly impaired in daily or vocational life. A further aspect is stereoscopic (3D) vision and binocular vision, whereby a person may not be able to perceive depth or may suffer from double vision, respectively.

Further important attributes of vision and subsequent types of vision testing are as follows:

SUMMARY

Detection Acuity

Detection acuity requires only the perception of presence or absence of an aspect of visual stimuli, not discrimination of the detail of the target presented. When used statically and peripherally, this forms the basis for peripheral field testing when the fixation is focused centrally and the stimulus presented in a peripheral location. In this regard, the result for each presentation of the stimulus is either 'seen' or 'unseen'.

When used centrally, detection acuity is used to define the smallest, or dimmest stimulus of light that can be detected, for a given wavelength for a given visual angle/distance, for a given background illuminance.

Another aspect of detection acuity is the ability to perceive the relative direction of movement of the stimulus or stimuli. Objects can be camouflaged to their background by use of luminance colour and texture. However the perception of motion with respect to the background is a useful indicator of visual function, at each end of its perceptual limit. The perception of movement can be impaired after brain damage, and thus perception of movement represents a function of higher cortical processing.

When measuring detection acuity; any one of contrast, colour, size or shape of the stimulus or the background, may be altered.

Resolution Acuity

In its simplest form, resolution acuity requires the visual system to discriminate if a gap is present between two stimuli. That is, if an area of brightness in the night sky is coming from a single star, or two stars separated by a small visual angle. This perception necessitates one unstimulated receptive area lies between two stimulated area. The visual angle denoted by the size of this unstimulated area relative to the stimulus distance, is directly relative to the spatial visual acuity measurement. Resolution acuity in this regard is the spatial resolving power of the visual system.

Preferential looking is form of resolution acuity. An optotype is a standardized symbol for testing vision. Vanishing optotypes are such symbols that are specifically designed to fade into the background when they are beyond the resolving power of the observing eye. Preferential looking is based on the inherent preference to look at a more detailed target, against a plain one. Gaze is inherently drawn to the target rather than the background, and the direction of the gaze change is used to make assumptions on the stimuli seen. Vanishing optotypes are a very different concept to an optotype that is removed from view, and is therefore not available for viewing even to a 'perfect' eye with infinite resolution. The advantage of vanishing optotypes is that they are more sensitive to optical defocus.

When measuring resolution acuity; any one of contrast, colour, size, texture or shape of the stimulus or the background, may be altered.

Recognition Acuity

Recognition acuity is the ability to discriminate detail of the target in order to recognize or name the target presented. Such an object is large enough that detection of the presence of the target is not a limiting factor. Examples of this type of acuity are reading aloud the letters on a typical eye chart, or matching the target image from a selection of reference images. When letters or symbols subtend a visual angle from the eye that is too small for the visual system to resolve the detail to sufficiently discriminate the pattern, the visual system is likely to still perceive that the stimulus is present. The best-known form of recognition acuity is that of the Snellen eye chart. Another core form of recognition acuity is that requiring a 'matching' exercise to a target symbol or letter.

Hyperacuity

Some aspects of visual perception can be judged with precision that is multiple times better than the spatial resolution of the visual system [visual acuity]. An example of such, Vernier acuity is the ability of the visual system to detect misalignment of two edges. Hyperacuity surpasses the resolution expected from the 'pixel density' of the retina and, in fact, represents neural summation in the visual brain and neural judgment of the localisation of the stimuli in visual space. When measuring hyperacuity; any one of contrast, colour, size, texture or shape of the stimulus or the background, may be altered.

Temporal Visual Acuity

Temporal visual acuity is the ability to distinguish visual events in time. One such event is the interpretation of presentation and removal of the stimulus. The presented repetition rate (flicker frequency) of a visual stimulus impacts upon the ease to which a said stimulus is detected by the human eye. In addition, the 'critical flicker fusion' rate is the frequency at which the flickering stimulus is perceived as a steady stimulus. The CFF is dependent upon the amplitude of the modulation of the illumination, the level to which the subject is light-adapted, the wavelength of the illumination and the retinal location of the stimulus. Any one of these factors may be altered in order to gain a clinical measure of the subjects temporal vision.

When measuring temporal visual acuity; any one of contrast, colour, size, texture or shape of the stimulus or the background, may be altered.

Spectral Acuity of Vision

Spectral acuity of vision is the ability to distinguish differences in the wavelength of stimuli, representing the extent of the accuracy of good colour discrimination. When measuring spectral visual acuity; any one of contrast, colour or size of the stimulus or the background, may be altered.

Visual Field

The visual field represents the vision that one perceives from the 'corners of the eyes'. The peripheral visual field is impaired by disease such as glaucoma, or stroke, whereby the patient may suffer from poor peripheral vision, or 'tunnel' vision, or have a chunk missing in a particular direction of their visual field. The central visual field is that contained in and around the line of sight and is perceived from the central retina, the macula.

The measure of resolution acuity, recognition acuity, hyperacuity and temporal acuity respectively require higher cortical processing on behalf of the patient than that required for simple detection or spectral acuity. The ability for a visual function testing system to measure more than one type of visual performance in one sitting, to elicit and analyse the differences in response between these two (and other) forms of visual responses is a key part in understanding not just the resolving power of the eye, but also the functioning of the visual system as a whole. The system of the present invention, therefore, provides medical as well as optical advantages.

'Staircase methods' working down from the largest letters or symbols to the smallest symbols are the traditional mode of practice. 'Vanishing optotypes' are symbols upon a carefully designed background that allow the symbol to disappear from view quickly after it is out of focus for the patient. This means that they cannot tell the location of the stimulus and so provide a negative response, or no response to the stimulus presented. This is the basis for 'preferential looking'—the technique used to measure the vision of pre-verbal children or non-verbal adults, with their eye movements observed rather than a verbal response being required in order to test vision. Inherently, humans will look at a stimulus that is more detailed than its background, but if it cannot be detected then the patient with simply perform a visual search for the object in question across the whole screen or presentation card.

The main record of vision is known as visual acuity. Whilst recognition visual acuity with the Snellen or Log MAR chart remains popular in clinical practice, it is widely known that the correlation of this measure alone with quality of life is poor compared to other measurements, such as contrast sensitivity and visual attention. This disparity exists due to the high contrast nature of traditional recognition visual acuity (VA). VA is defined by the smallest identified measure at maximal contrast (black and white)—this is now recognized in the scientific community as a very artificial arrangement. However, this does not represent real-world visual perception, since very little that we see is truly black and white, but rather a continuum of grey and colour. Measurement of the central vision utilising colour and/or contrast and the dynamic presentation of stimuli, such as that which is moving, or flickering, better approximates real-world visual experience than that of a traditional test chart.

Visual acuity is traditionally measured on a Snellen chart at 6 m or 20 feet. The patient reads down the chart until they cannot read the letters clearly and the last line of letters read correctly is recorded. If a line is partially read, this is accounted for with further annotation. Research based measures of vision use a log MAR based system, where the letters are more regular in shape and in layout, with there being an equal number of letters on each line, and with equal spacing between letters and between lines. This makes a log MAR chart more sensitive to real changes in vision and thus more reliable in a clinical or a research environment. Yet, for reasons of convention and tradition, most clinicians (such as doctors, opticians, nurses) have not yet moved towards measuring vision on a log MAR chart from Snellen, and the perception to conversion of the notation is difficult. Therefore any device which assists in this conversion is a contribution to eye care.

In clinical practice, contrast sensitivity is measured (albeit infrequently) on a Pelli Robson Chart. This chart provides blocks of 3 letters in a fixed letter size in varying contrasts down the chart until the letters fade to the background and are seen to disappear. Whilst simple and easy, the Pelli Robson chart is rarely used by clinicians largely due to availability, perceived usefulness and time restrictions. In research, a computer based system is used to present such stimuli in a manner (systematic or randomized) until the threshold of greatest sensitivity is reached. This is time consuming and uninteresting for the patient.

Colour vision is a vital visual measurement in neurological examination and in the screening for inherited colour vision defects in children. It may be measured in clinical practice using isochromatic plates from the Ishihara screening test (by the reading aloud of numbers) or a City University colour vision test or a D-15 colour test (arranging colours in order of hue). In research, or in more sensitive clinical testing environments, colour vision is measured using the Farnsworth Munsell 100 hue test. Whilst more sensitive, it is time consuming and not practical for clinical use.

Downloadable smartphone/tablet vision tests are known. However, these are not provided in a gaming environment or setting and do not allow automatic representation of near-threshold stimuli. They do not measure more than one aspect of vision in one sitting. These known systems only measure one aspect of visual functioning in one sitting and are not designed to test the plurality of visual function as described above. They are rarely clinically validated and thus are not appropriate for monitoring patients with, or at risk of specific eye disease.

Other designs of digital measurement of visual functioning focus on altering the size of the optotype or target with respect to the viewing distance; and in order to increase the task difficulty. Rather, this invention utilises changes in the detail of the stimulus rather than the its size.

With the huge surge in medical and genetic therapies in ophthalmology, eye departments are overwhelmed with the need to follow-up and monitor stable patients. Demand for eye clinic appointments frequently outstrips current supply. The need arises for a device that is able to measure vision accurately and quickly, using an intelligent threshold algorithm, such that it is suitable even for young children or those with dementia. There is a need for a solution which provides the user with an indication of visual performance with respect to that of the general population, or with respect to their usual functioning in that eye.

Thus, it is desirable to provide an automated solution which enables the accurate measurement of a patient's vision in a format which is engaging for the patient and easy to use, and that measures visual function comprehensively, rather than a single measure of detection or recognition acuity alone. Such a solution may provide a platform which measures vision based on a distraction method. It may also measure eye movement to validate the optotype seen by the patient. It may also measure the different facets of vision in one sitting, such as visual acuity (VA), contrast sensitivity, colour vision, central visual field and stereopsis. Another objective of such a solution may be to utilise a gaming environment in order measure vision. This testing may be performed or achieved in a way that is hidden from the patient. This can enable the identification of those who are malingering, or being untruthful about their level of vision, in an objective way.

Such an improved solution has now been devised. The invention is defined in the appended claims.

In accordance with the invention there may be provided a system for measuring a plurality of aspects of vision. Herein, the terms 'visual function' and/or 'visual performance' may be used interchangeably with the term 'vision'. The system may comprise a computing device arranged and configured to:

present at least one optotype to a user within a gamified environment, the optotype having at least one characteristic selected to facilitate the measurement of at least one aspect of visual function, or at least two aspects of visual function; and detect the user's response to the optotype to provide a measurement of at least one aspect of visual function. In some embodiments, the invention provides a measurement of at least two aspects of visual function.

The aspect(s) of visual function may be measured within one sitting. A 'sitting' may be a session of use of the invention, or a presentation or part thereof to the user.

The optotype may be selected to facilitate the measurement of the at least two aspects of visual function within one sitting. The invention may be arranged to detect the user's response to the optotype to provide a measurement of the at least two aspects of visual function within one sitting.

The invention may be arranged to measure the visual function of both of the user's eyes. The visual function of both eyes may be measured simultaneously. Additionally or alternatively, the invention may be arranged to measure the visual function of each eye separately. In the latter case, an occlusive device may be used in respect of the fellow eye.

Preferably, the invention may be a game-based solution (comprising methods and apparatus) for measuring and/or testing a plurality of aspects of visual function. It may test/measure the user's visual response to the optotype.

A plurality of optoptypes may be presented to the user. Each optoptype may have one or more characteristics associated with it, each selected to facilitate the measurement of at least one aspect of visual function. Alternatively, one optotype may be presented, the optotype having a plurality of characteristics, each selected (prior to starting the test) to facilitate the measurement of at least one, but preferably multiple, aspects of visual function. In this way, the invention is able to measure a plurality of aspects of visual function in one presentation to the user ie one test or 'sitting'.

Presentation of the optoptype may be in a visual form ie displayed on a display device. The optotype may provide a visual stimulus. The computing device may be a handheld device such as a tablet computer or a smartphone. The device may have a screen associated with it. It may be a touchscreen. It may have an integral camera. Such devices have the advantage of being low cost and in common use.

The device may comprise one or more software and/or hardware components arranged to provide the functionality of the present invention. One or more software components may be downloaded to the device for installation thereon, and for subsequent execution of the gamified measuring tool. The software may be downloaded from a remote location, such as a server. It may be downloaded from the cloud. The software may be an app-based solution.

The invention may be used to measure visual function from both eyes together, and each eye separately using an occlusive device on the fellow eye.

Advantageously, the computer-implemented invention may be able to measure a plurality of aspects of visual function (performance). This is not only challenging from a technical perspective but provides a more informative assessment of the user's vision. The measurement(s) may be stored on the device and/or sent to a remote device such as a server.

The measurement(s) captured by the invention may be automated in that the intervention of a clinical or trained practitioner is not required. This provides the advantage that the invention can be used at home, for example, without the need for a clinical expert to be present.

The invention may be arranged to present at least one optotype to a user within a gamified environment. Thus, the vision test is presented to the user as an electronic game or in a game-type format. The user may be able to interact with the game in one or more ways. For example, user input can be captured via a touch screen, eye or motion tracking technology, or via a microphone. Presentation of the optotype may be provided on a screen associated with the device. Thus, the invention may provide a game based approach to measuring aspects of the user's vision. This provides an interesting, engaging environment which is desirable for a user to interact with, and is suitable for use with patients of different ages and intellectual/physical abilities eg young children or those with disabilities. The user may not even be aware that a vision test is being conducted as they use the invention.

The optotype may have at least one characteristic selected to facilitate the measurement of at least one, but preferably multiple, aspects of visual function. This characteristic may relate to the detail provided in association with the optotype, the location, size, colour and/or brightness of the optotype. It may relate to the movement of the optotype such as its speed and/or direction of travel. Thus, the optoptype may be pre-selected ie prior to initiation of the test such that it is carefully chosen to exhibit attributes or qualities which enable a measurement of an aspect of visual function to be generated.

The system may be configured to present a vanishing optotype to the user, and/or use preferential looking.

The plurality of aspects of visual function may include, for example, (one or more of) detection acuity, resolution acuity, recognition acuity, hyperacuity, temporal acuity, spectral acuity, visual acuity, central visual field, contrast sensitivity, stereopsis and/or colour vision. Preferably, more than one of these aspects is measured by the invention.

This is an improvement over prior art systems which only measure one aspect of visual functioning eg solely detection acuity (measuring the movement of eyes towards a peripheral stimulus) or solely recognition acuity (measuring the ability to 'match to a target symbol').

The system may be arranged and configured to repeatedly present the at least one optotype to the user. Preferably, the at least one characteristic is altered upon each repetition. For example, the optotype may be reduced in size, or appear in a different colour upon subsequent display of the optotype on the screen.

The invention may implement a stair-casing approach to vision testing and measurement. The system may be arranged and configured to repeatedly present the at least one optotype until a threshold or limit is reached. The threshold or limit may relate to the user's head and/or eye movement or position. For example, if the system detects that the user's eyes are no longer looking at the screen, this may indicate that the user can no longer see the optotype, has lost interest as a result and is no longer engaging with the software on the device.

Each presentation may present a modification to a different aspect of the stimulus. The change characteristic may relate to the level of detail, contrast, colour, position, timing and/or movement of the at least one optotype. Thus, through a session of gameplay with multiple presentations of stimuli, the invention may combine more than one aspect of vision into a single test. Therefore, it provides a more accurate representation of visual function, and a more reliable testing technique than the prior art solutions since the visual processing is being measured on more than one cognitive level. It also provides a more accurate, reliable and swifter testing technique than the prior art solutions.

The system may be arranged and configured to detect the distance of the computing device from the user, preferably from the user's eyes or face. Additionally or alternatively, it may be able to detect forward or backward movement of the device relative to the user. Therefore, the device may be capable of detecting and measuring how far away it is from the user. This distance may change over time as the user manipulates the handheld device to move it closer or further away, and the device may detect this change in relative position. This distance may be stored in memory as a measurement. A dynamic measurement of vision may thus be captured. The detail (e.g. granularity) within the shape of the presenting optotype may be altered in order to compensate for the change in viewing distance, and thus make the invention less prone to human error. The optotype may be removed from gameplay if the device is beyond the tolerance of a suitable viewing distance.

The system may be arranged and configured to track the user's eye or head movement, speed of movement of the user's eye(s), and/or location of the user's eyes or gaze relative to the device or a portion thereof. Eye and body tracking techniques are known in the art. By incorporating such technology into the device, the present invention is able to detect where the user is looking and what they are looking at. For example, the invention is able to detect whether the user has observed the correct optoptype. Conversely, if their eyes are wandering around or looking elsewhere then the optotype has not been observed. It may be deduced that the user is unable to see the optotype.

The system may be configured to provide feedback to the user upon identification of at least one pre-determined optotype. Therefore, the user may be provided with a 'reward' for correctly identifying the optotype or a characteristic thereof. The in-game, performance related feedback may be provided in visual, audible and/or tactile form. The feedback may be provided upon identification of the at least one pre-determined optotype by touching or looking at a portion of a screen associated with the computing device, or eye movement toward the optotype at a predetermined or calculated speed.

The system may be further configured to compare the measurement against a normative database comprising age-matched visual performance data. The database may comprise data which is organised relative to age, and represents expected or normal measurements for persons of a given age. The invention may collect data for the database over time. Thus, the database provides a reference against which the user's measurements can be compared to determine whether aspect(s) of the user's vision fall within a clinically acceptable range for their age. The comparison may be performed on the computing device itself or on a remote device such as a server. The database may be provided on the computing device or on a server.

Feedback relating to the comparison may be transmitted or presented to the user and/or another destination. For example, it may be sent to the user's medical team, or emailed to an email address, or displayed on a screen. This feedback may be referred to as 'normative feedback' to distinguish it from the feedback provided during the game itself, as described above.

Therefore, the invention may collect data for the database over time. The database may be provided on the computing device or on a server. The system may be configured such that the measurements may be able to be relayed back to the user, in terms of how their visual performance in that eye relates to that of a normative population, or how their visual performance relates to their performance on previous occasion(s). The comparison may be performed on the computing device itself or on a remote device such as a server. The user may be informed if a change in their visual performance requires a visit to an eye care professional. The user may have the opportunity to share the details of their visual performance with health care professionals. For example, it may be automatically sent to the user's medical team, or emailed to an email address, or displayed on a screen.

Thus, the invention provides a solution which enables individuals to test visual abilities or characteristics thereof and obtain some feedback as to whether the results indicate that there is a problem with some aspect of visual function. As the invention can be used anywhere, without the intervention of a trained expert, it is well suited for use by parents for testing their children's visual function, or by other carers.

If the feedback indicates that there may be a problem, the user can be referred to an expert for further investigation or treatment. Thus, the invention may not provide a diagnosis technique. Instead, it may provide a measuring tool or apparatus for capturing data relating to aspects of visual function, which can then be provided to an expert for subsequent use in diagnosis.

The system may be arranged to store data relating to the captured measurement(s). This may enable the user's current visual function to be compared to previously recorded measurements and thus enable indications or conclusions to be drawn as to the reliability of the measurements and/or any change in the user's visual function over time.

A corresponding method is also provided. Any feature described above in relation to the system may also be applicable in relation to the method and vice versa.

Thus, the invention may provide a method for measuring a plurality of aspects of vision (visual function), the method comprising the steps:
presenting at least one optotype to a user within a gamified environment on a computing device, the optotype having at least one characteristic selected to facilitate the measurement of at least one aspect of vision or at least two aspects of visual function; and detecting the user's response to the optotype to provide a measurement of at least one or at least two aspects of vision.

The aspect(s) of visual function may be measured within one sitting. A 'sitting' may be a session or part of a session of use. It may be one game. It may be one iteration or performance of a test or part of a test.

Preferably, the invention provides a game based solution for measuring and/or testing a plurality of aspects of visual function. It may measure/test the user's visual response.

The computing device may be a portable and/or handled device. The plurality of aspects of vision may include one or more of: visual acuity, central visual field, contrast sensitivity, stereopsis and/or colour vision, detection acuity, resolution acuity (spatial resolution or identification of static of dynamic directionality), recognition acuity, hyperacuity, temporal acuity, spectral acuity.

The method may include the step of repeatedly presenting the at least one optotype to the user, wherein the at least one characteristic is altered upon each repetition. It may include the step of repeatedly presenting the at least one optotype until a threshold or limit is reached.

The at least one characteristic may relate to the level of detail (granularity), contrast, colour, position or movement of the at least one optotype.

The method may include the step of detecting the distance of the computing device from the user, preferably from the user's eyes or face; and/or detecting forward or backward movement of the device relative to the user. It may include the step of tracking the user's eye or head movement, speed of movement of the user's eye(s), and/or location of the user's eyes or gaze relative to the device or a portion thereof.

The method may include the step of comparing the measurement against a normative database comprising age-matched visual performance data and/or normative data for a given stage of a disease.

The method may include the step of presenting a vanishing optotype to the user.

The method may include the step of providing feedback to the user upon identification of at least one pre-determined optotype. The feedback may be provided in visual, audible and/or tactile form. The feedback may be provided upon identification of the at least one pre-determined optotype by touching or looking at a portion of a screen associated with the computing device, or eye movement toward the optotype at a predetermined speed.

The invention may provide a system for measuring a plurality of aspects of visual function, the system comprising a handheld computing device arranged and configured to:
present at least one optotype to a user within a gamified environment, the optotype having at least one characteristic selected to facilitate the measurement of at least one aspect or at least two aspects of vision;
detect the user's response to the optotype to provide a measurement of at least one aspect of vision; and
configured to compare the measurement against a normative database comprising age-matched visual performance data.

The invention may provide a method for measuring a plurality of aspects of visual function, the method comprising the steps:
presenting at least one optotype to a user within a gamified environment on a computing device, the optotype having at least one characteristic selected to facilitate the measurement of at least one aspect or at least two aspects of visual function; and
detecting the user's response to the optotype to provide a measurement of at least one or at least two aspects of visual function; and
comparing the measurement against a normative database comprising age-matched visual performance data.

The invention may provide a system for measuring a plurality of aspects of visual function, the system comprising a handheld computing device arranged and configured to:
present at least one optotype to a user within a gamified environment, the optotype having at least one characteristic selected to facilitate the measurement of at least one or at least two aspects of visual function;

detect the user's response to the optotype to provide a measurement of at least one or at least two aspects of vision by tracking the user's eye or head movement, speed of movement of the user's eye(s), and/or location of the user's eyes or gaze relative to the device or a portion thereof.

The invention may provide a method for measuring a plurality of aspects of visual function, the method comprising the steps of:

presenting at least one optotype to a user within a gamified environment on a handheld computing device, the optotype having at least one characteristic selected to facilitate the measurement of at least one aspect or at least two aspects of visual function;

detecting the user's response to the optotype to provide a measurement of at least one aspect or at least two aspects of visual function by tracking the user's eye or head movement, speed of movement of the user's eye(s), and/or location of the user's eyes or gaze relative to the device or a portion thereof.

Any feature(s) described in relation to one aspect or embodiment of the invention may be applicable to one or other aspects or embodiments of the invention but may not be repeated for the sake of clarity. Any feature(s) mentioned in respect of a method of the invention may be used in relation to a system of the invention, or vice versa.

These and other aspects of the present invention will be apparent from and elucidated with reference to, the embodiment described herein. An embodiment of the present invention will now be described, by way of example, and with reference to the accompanying drawings.

DETAILED DESCRIPTION

Various aspects and embodiments of the invention provide an automated measurement of a patient's vision. Not only is the measurement produced by the invention more accurate than the results provided by prior art arrangements, but the invention enables self-administration without the need for expert intervention. The invention provides a platform which measures multiple aspects of vision based on a distraction method. Some embodiments track or detect eye and/or head movement to validate the optotype seen by the patient (ie user). Advantageously, the different facets of vision can be measured in one sitting.

The aspects of visual function which can be measured by the invention may include visual acuity, colour vision, contrast sensitivity, central visual field and/or stereopsis.

Measurements of the visual aspects are captured by the detection and/or recording of a positive, absent or negative response to a presented stimulus (optotype). The stimuli are pre-determined to correlate to an established level of vision for visual acuity, contrast sensitivity, colour perception etc. The algorithm is able to adapt the presentation for each repetition depending upon the response to a previous stimuli and present subsequent stimuli (optotypes) accordingly, in order to reach the threshold values as soon as possible. This threshold value, or near-threshold value, can be re-presented intermingled with known above-threshold and known below-threshold stimuli in order to maintain interest and to gain a measure of patient reliability using false positive and false negative indicators.

The invention delivers the vision test to the user via a game format wherein optotypes are presented as part of this game or activity. The games process means that the patient is often unaware that their vision is being measured, and such a format assists in maintaining the user's interest.

The optotypes included in the game, and the way they are presented, are carefully selected so as to present objects which exhibit certain features or attributes that enable the computing device to capture measurements of vision. For example, a plurality of optotypes may be presented but one optoptype may be brighter compared with the background, may move across the screen at a certain speed, or may be of a certain size or colour. The user's visual response to the optotypes can be detected by the invention and the measurement captured and stored. For example, if the user looks at the brightest optotype this can be detected. The user has been able to select one particular optotype and distinguish it from the others.

Capture of the measurement can be performed by motion tracking technology. The user's eye movement or head movement can be detected so as to determined whether the user has seen the optotype and how their vision is functioning with regard to a particular aspect. Tracking head movement in response to a different location of optotype can be detected and stored as a measurement.

Computer vision technologies may also be incorporated to enable the invention to dynamically detect how far the user's face is from the device. This provides a more accurate measurement. Therefore, the invention can detect whether the user is moving the device forward and/or backward in order to aid vision. This can be used to generate a measurement of visual ability.

The game or activity repeatedly presents the optoptypes to the user with varying characteristics. For example, the optotype can be shown in increasingly smaller size until the invention detects that the user is unable to see it. This provides the ability retest at the threshold until the measurement is deemed to be reliable.

Thus, the invention can be used to implement vanishing optotypes and/or preferential looking on a handheld computing device such as a tablet.

The invention also provides the ability to store and compare measurements over time. This enables statistical or relevant changes in vision to be detected, making on-going monitoring of an individual's vision more effective.

Moreover, the collection of data from multiple users enables the generation and evolution of a reference database, which can give age-matched norms. This is an advantageous feature of the invention because it allows for an indication of whether a particular individual's vision is normal for their age. If the comparison with the reference data indicates that there may be a problem with an aspect of their vision, an alert can be generated prompting clinical or expert investigation.

In use, the invention may be utilised in different 'modes':
1—Home testing—monitoring mode
2—Primary care testing—screening mode
3—Secondary care testing—diagnostic mode The different modes may have a subset for age matched and disability standards. For example, younger patients or disabled patients may have a slower progression through the game.

Upon first interaction with the system, the user may need to register. User-related data bay be captured, such as identifier data, name, date of birth. The system may also be implemented to include facial recognition of the user. Facial recognition technologies are known. After initial log in, this set up would not need to be repeated as the machine will be able to recognise the user.

Once logged in, the user is presented with the game or activity. The optotype will vary in detail, contrast, colour, position and/or motion.

Figure 1:
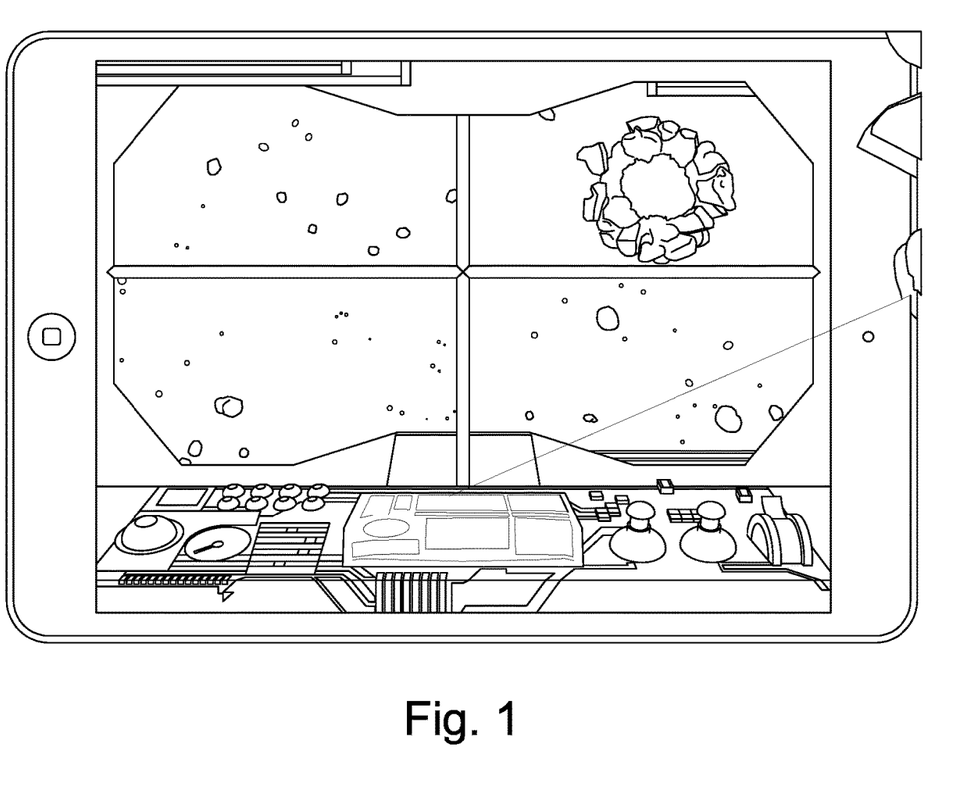
FIG. 1 shows a screen presenting a gamified visual measuring tool in accordance with an embodiment of the invention.

As shown in the example of FIG. 1, the screen may be divided into 4 quadrants. In one embodiment, different optotypes are presented in respective quadrants. For example, a particular optotype, having certain characteristic (s) is presented in one quadrant. For example, in FIG. 1, the top right quadrant includes an optotype (in this example, a meteorite) which is brighter and larger than the others.

If the optotype is identified in the correct location by the user there is a visual (exploding optotype), sound (explosion sound) and tactile reward (vibrating tablet). The correct optotype can be identified by either 1—touch
2—location on the screen by eye movement
3—a movement toward the optotype of a certain speed of eye movement.

Then another screen is presented with varied optotypes. For example, the meteorite may now be in a different quadrant, and may be smaller, or of a higher granularity, more detailed, and/or less bright than previously presented. This process is repeated until a threshold is reached for all variables. Upon conclusion of the game, the threshold of vision for each facet of visual performance has been obtained.

Figure 2:
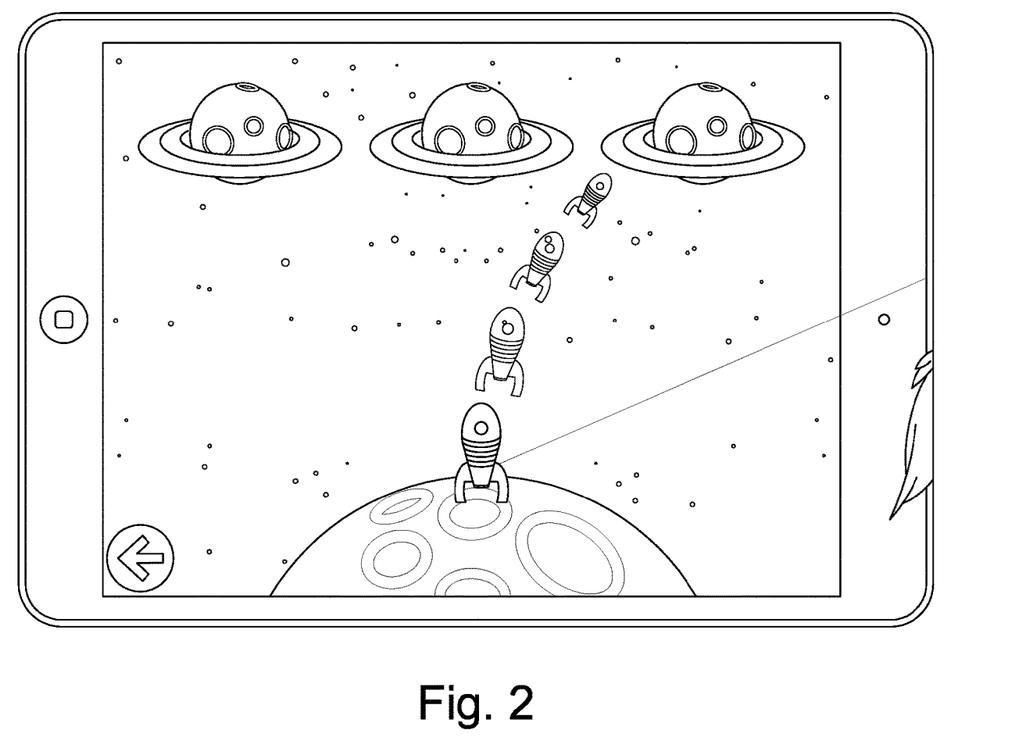
FIG. 2 shows an alternative version of a screen presenting a gamified visual measuring tool in accordance with an embodiment of the invention.

In other embodiments the game may not be confined to 4 equal squares or quadrants. In FIG. 2, a rocket is fired towards the 'correct' ('matching' target) optotype when the user visually selects it. There will be a resultant 'reward' in the form of a visual (exploding optotype), sound (explosion sound) and tactile reward (vibrating tablet).

Thus, embodiments and aspects of the invention provide a system which overcomes the difficulties associated with prior art arrangements by:

1. Providing a 'game' interface that the patient interacts with; thus, the patient is unaware of which aspect of vision is being measured;
2. It does not require the use of letters or matching symbols which are unsuitable for very young, or intellectually disabled patients;
3. Allowing repeated testing of visual threshold using a dynamic staircase approach which maintains attention;
4. Measuring more than one aspect of vision within the same sitting, thereby providing a more relevant measure of vision than just visual acuity. This provides the clinician with more information about the likely quality of vision, and about how well the patient is able to use their vision on a functional level
5. Does not require the intervention of an expert or trained operator, and so can be used in a variety of environments; for example, a parent can use it to test their child's vision;
6. It can be used to measure aspects of vision in patients who are not able to communicate well verbally eg children, the disabled because the invention is able to detect and measure visual performance in an automated manner;
7. Storing data which can then be compared to previous records and to age and condition matched norms, allowing any statistically/clinically significant deviations to the expected values to be reported to the patient and/or the responsible eye care professional.

Importantly, the vision measuring solution provided by the invention enables patients to monitor their vision at home, rather than in a clinical setting, and in a way that is fast, reliable and prevents 'cheating'. Patient identity may be maintained through the use of face recognition/fingerprint analysis. Additionally or alternatively, a code, password or other identifier can be used to identify the patient.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. In the present specification, "comprises" means "includes or consists of" and "comprising" means "including or consisting of". The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for measuring a plurality of aspects of visual function, the system comprising:
   a handheld computing device arranged and configured to:
      present at least one optotype to a user on a background within a gamified environment, the optotype having at least one characteristic selected to facilitate the measurement of resolution acuity and at least one other aspect of visual function; and
      detect the user's response to the optotypes to provide a measurement of resolution acuity and at least one aspect of visual function,
   wherein the at least one optotype comprises one or more vanishing optotypes, wherein the system is arranged and configured to repeatedly present the one or more vanishing optotypes to the user, and the position and at least one other characteristic of each optotype is altered upon each repetition, such that the one or more optotypes are configured to fade into the background when they are beyond the resolving power of the user's eye.

2. The system according to claim 1, wherein:
   the at least one other aspect of visual function include visual acuity, central visual field, contrast sensitivity, stereopsis, color vision, detection acuity of vision, recognition acuity of vision, hyperacuity of vision, temporal acuity of vision, spectral acuity of vision.

3. The system according to claim 1, wherein:
   the at least one characteristic relates to the level of detail, contrast, color, position or movement of the at least one optotype.

4. The system according to claim 1, wherein: the system is arranged and configured to detect at least one of:
   distance of the computing device from the user; and
   forward or backward movement of the device relative to the user.

5. The system according to claim 1, wherein: the system is arranged and configured to:

track the user's eye or head movement, speed of movement of the user's eye(s), and/or location of the user's eyes or gaze relative to the device or a portion thereof.

6. The system according to claim 1, wherein: the system is further configured to compare the measurement against a normative database comprising age-matched visual performance data.

7. The system according to claim 1, wherein: the system is configured to provide
feedback to the user upon identification of at least one pre-determined optotype.

8. The system according to claim 7, wherein:
the feedback is provided upon identification of the at least one pre-determined optotype by touching or looking at a portion of a screen associated with the computing device, or eye movement toward the optotype at a predetermined speed.

9. The system according to claim 1, wherein the system is configured to store data relating to the measurement to enable the user's current visual function to be compared to previously stored measurements.

10. A method for measuring a plurality of aspects of visual function, the method comprising:
presenting at least one optotype to a user on a background within a gamified environment on a handheld computing device, the optotype having at least one characteristic selected to facilitate the measurement of resolution acuity and at least one other aspect of visual function; and
detecting the user's response to the optotype to provide a measurement of resolution acuity and at least one other aspect of visual function,
wherein the at least one optotype comprises one or more vanishing optotypes, wherein the one or more vanishing optotypes are repeatedly presented to the user, and the position and at least one other characteristic of each optotype is altered upon each repetition, such that the one or more optotypes are configured to fade into the background when they are beyond the resolving power of the user's eye.

11. The method according to claim 10, wherein:
the at least one other aspect of visual function includes visual acuity, contrast sensitivity, stereopsis, central visual field, color vision, detection acuity of vision, recognition acuity of vision, hyperacuity of vision, temporal acuity of vision, spectral acuity of vision.

12. The method according to claim 10, further comprising at least one of:
repeatedly presenting the at least one optotype until a threshold or limit is reached; and
detecting the distance of the computing device from the user.

13. The method according to claim 10, further comprising at least one of:

i) tracking the user's eye or head movement, speed of movement of the user's eye(s), and/or location of the user's eyes or gaze relative to the device or a portion thereof; and
ii) comparing the measurement against a normative database comprising age-matched visual performance data or normative data for the known stage of disease.

14. The method according to claim 10, further comprising:
providing feedback to the user upon identification of at least one pre-determined optotype.

15. The method according to claim 14, wherein:
the feedback is provided upon identification of the at least one optotype by touching or looking at a portion of a screen associated with the computing device, or eye movement toward the optotype at a predetermined speed.

16. The method according to claim 10, further comprising:
storing data relating to the measurement to enable the user's current vision to be compared to previously stored measurements.

17. The system according to claim 3, wherein:
the system is configured to repeatedly present the at least one optotype until a threshold or limit is reached.

18. The system according to claim 4, wherein:
the system is arranged and configured to detect distance of the computing device from the user's eyes or face.

19. The system according to claim 7, wherein:
the feedback is provided in at least one of visual, audible, and tactile form.

20. The method according to claim 12, wherein:
the at least one characteristic relates to the level of detail, contrast, colour, position or movement of the at least one optotype.

21. The method according claim 14, wherein:
the feedback is provided in visual, audible and/or tactile form.

22. The system according to claim 1, wherein:
the vanishing optotypes are intermingled with optotypes which are known to be above and/or below the resolving power of the user's eye.

23. The system according to claim 10, wherein:
the vanishing optotypes are intermingled with optotypes which are known to be above and/or below the resolving power of the user's eye.

24. The system according to claim 1, wherein:
the at least one optotype comprises a plurality of vanishing optotypes presented on the background at the same time.

25. The method according to claim 10, wherein:
the at least one optotype comprises a plurality of vanishing optotypes presented on the background at the same time.

* * * * *